US012667333B2

(12) United States Patent
Howard et al.

(10) Patent No.: US 12,667,333 B2
(45) Date of Patent: *Jun. 30, 2026

(54) DISPLAYING DATA BASED ON MACHINE-READING OF AN ULTRASOUND DEVICE

(71) Applicant: FUJIFILM SONOSITE, INC., Bothell, WA (US)

(72) Inventors: Christopher Howard, Seattle, WA (US); Craig Chamberlain, Seattle, WA (US); Jimin Zhang, Bellevue, WA (US); Katsuya Yamamoto, Kanagawa (JP); Andrew Lundberg, Woodinville, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 173 days.

This patent is subject to a terminal disclaimer.

(21) Appl. No.: 18/344,346

(22) Filed: Jun. 29, 2023

(65) Prior Publication Data

US 2025/0000486 A1 Jan. 2, 2025

(51) Int. Cl.
| | |
|---|---|
| *G06K 7/10* | (2006.01) |
| *A61B 8/00* | (2006.01) |
| *G06F 16/955* | (2019.01) |
| *G06K 19/06* | (2006.01) |
| *G01S 7/52* | (2006.01) |

(52) U.S. Cl.
CPC .......... *A61B 8/4438* (2013.01); *A61B 8/4433* (2013.01); *A61B 8/461* (2013.01); *A61B 8/56* (2013.01); *G06F 16/9554* (2019.01); *G06K*
*19/06112* (2013.01); *G01S 7/52057* (2013.01); *G01S 7/52084* (2013.01); *G01S 7/52098* (2013.01)

(58) Field of Classification Search
CPC ..... A61B 8/462; A61B 8/4263; A61B 8/4411; A61B 8/4438; A61B 8/4472; A61B 8/4488; A61B 8/56; A61B 90/98; A61B 2090/3904; A61B 2090/3945; A61B 2090/365; A61B 2034/2063; A61B 2034/2065; A61B 8/4433; A61B 8/461; G06F 16/9554; G06K 19/06112
USPC .................................................... 235/462.01
See application file for complete search history.

(56) References Cited

U.S. PATENT DOCUMENTS

| | | | | |
|---|---|---|---|---|
| 8,721,344 | B2 * | 5/2014 | Marmaropoulos .... | A63H 30/00 434/262 |
| 11,372,093 | B2 | 6/2022 | Lundberg et al. | |
| 12,350,102 | B2 * | 7/2025 | Nally ........................ | A61B 8/56 |
| 2016/0256101 | A1 * | 9/2016 | Aharoni ............... | A61B 5/0086 |
| 2019/0206562 | A1 * | 7/2019 | Shelton, IV ......... | H04N 23/555 |
| 2019/0374199 | A1 * | 12/2019 | Griffith ................ | A61B 8/4427 |

(Continued)

*Primary Examiner* — Daniel St Cyr
(74) *Attorney, Agent, or Firm* — Womble Bond Dickinson (US) LLP

(57) ABSTRACT

Systems and methods for displaying data based on machine-reading of an ultrasound device are described. In some embodiments, an ultrasound system includes an ultrasound device having a machine-readable indicator and a reader device configured to read information from the machine-readable indicator. The ultrasound system also includes a display device configured to display device information about the ultrasound device based on the information read from the machine-readable indicator.

18 Claims, 11 Drawing Sheets

(56) References Cited

U.S. PATENT DOCUMENTS

| | | | |
|---|---|---|---|
| 2019/0374200 A1* | 12/2019 | Griffith | A61B 8/4427 |
| 2019/0374201 A1* | 12/2019 | Griffith | A61B 8/4427 |
| 2020/0142942 A1* | 5/2020 | Peri | H04L 65/1069 |
| 2022/0175347 A1* | 6/2022 | Li | G16H 40/67 |
| 2022/0287676 A1* | 9/2022 | Steines | A61B 90/37 |
| 2023/0389893 A1* | 12/2023 | Misener | A61B 8/4444 |
| 2024/0115238 A1* | 4/2024 | Nally | A61B 8/0891 |

* cited by examiner

100

101

Ultrasound Device

Ultrasound Device

102

Machine-Readable Indicator

103

Shadow of Reader Device

104

Augmented Reality Displayed on Reader Device and Overlaid on Ultrasound Device

105

Visual Representation

106

107

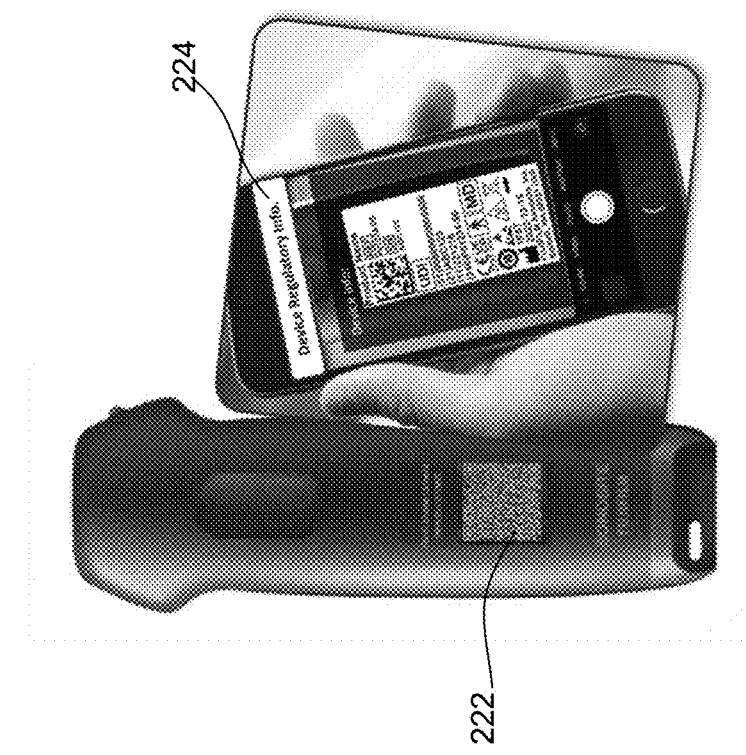
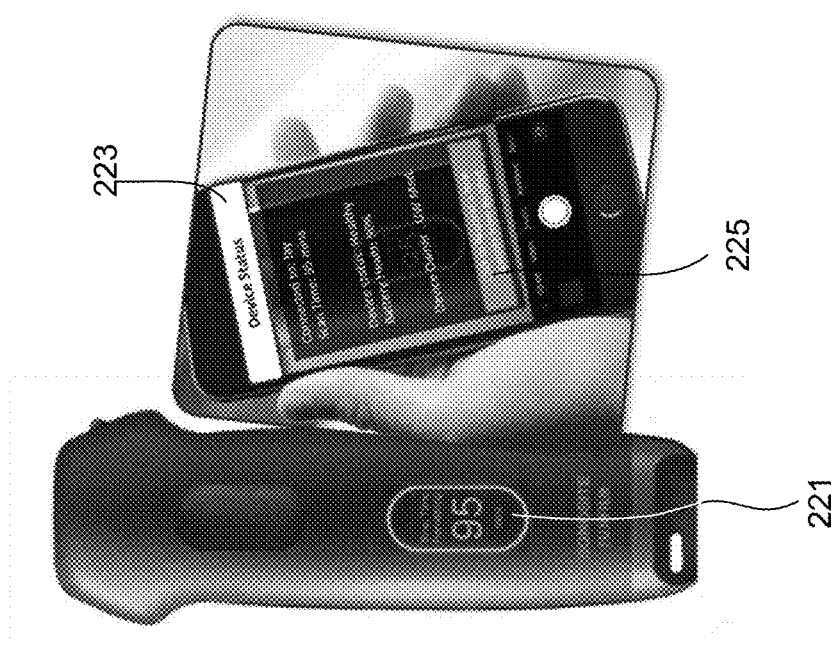
FIG. 2B

230

236

234

233

232

231

235

300

400

Figure 5:
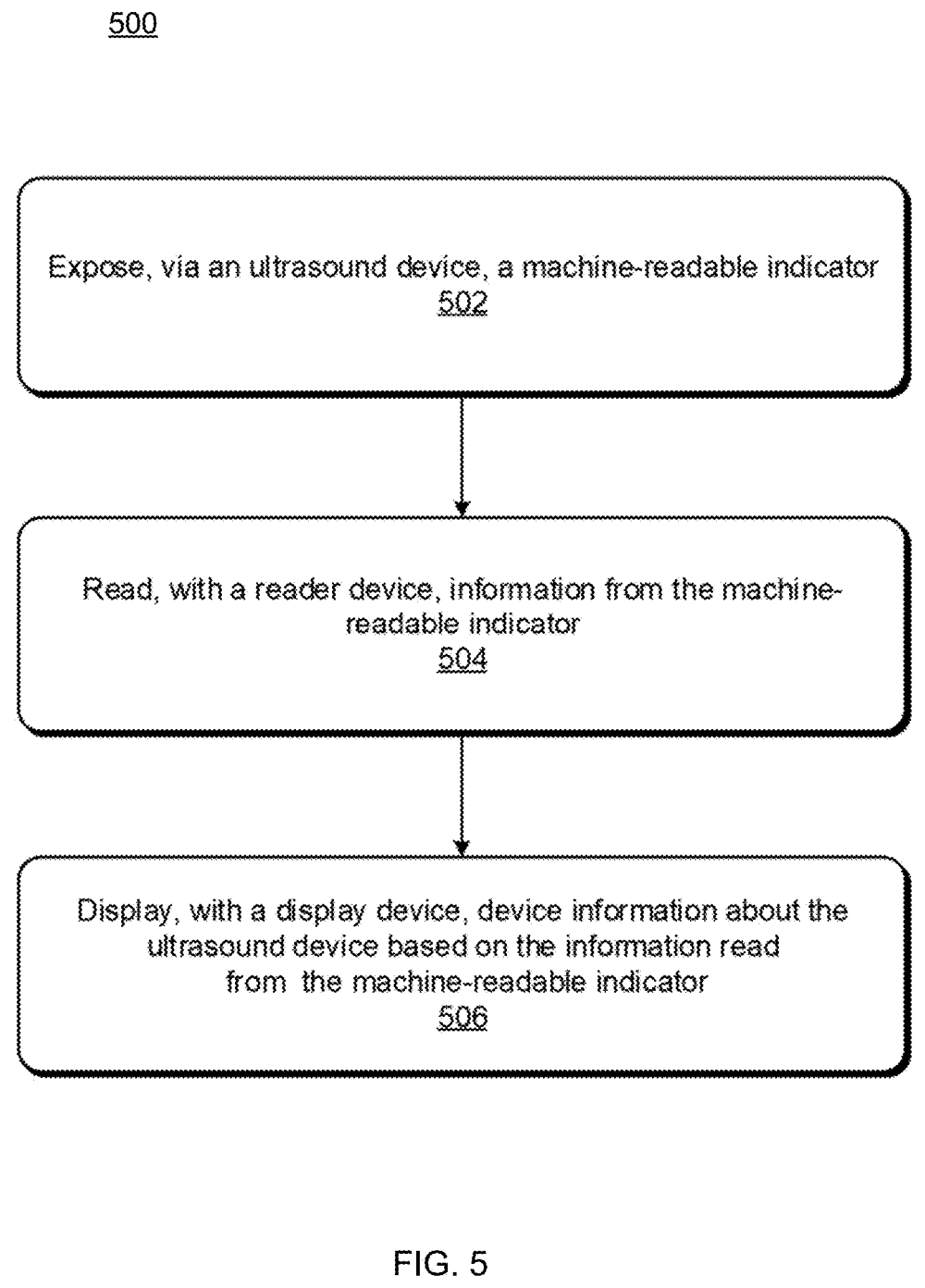

500

Expose, via an ultrasound device, a machine-readable indicator
502

Read, with a reader device, information from the machine-readable indicator
504

Display, with a display device, device information about the ultrasound device based on the information read from the machine-readable indicator
506

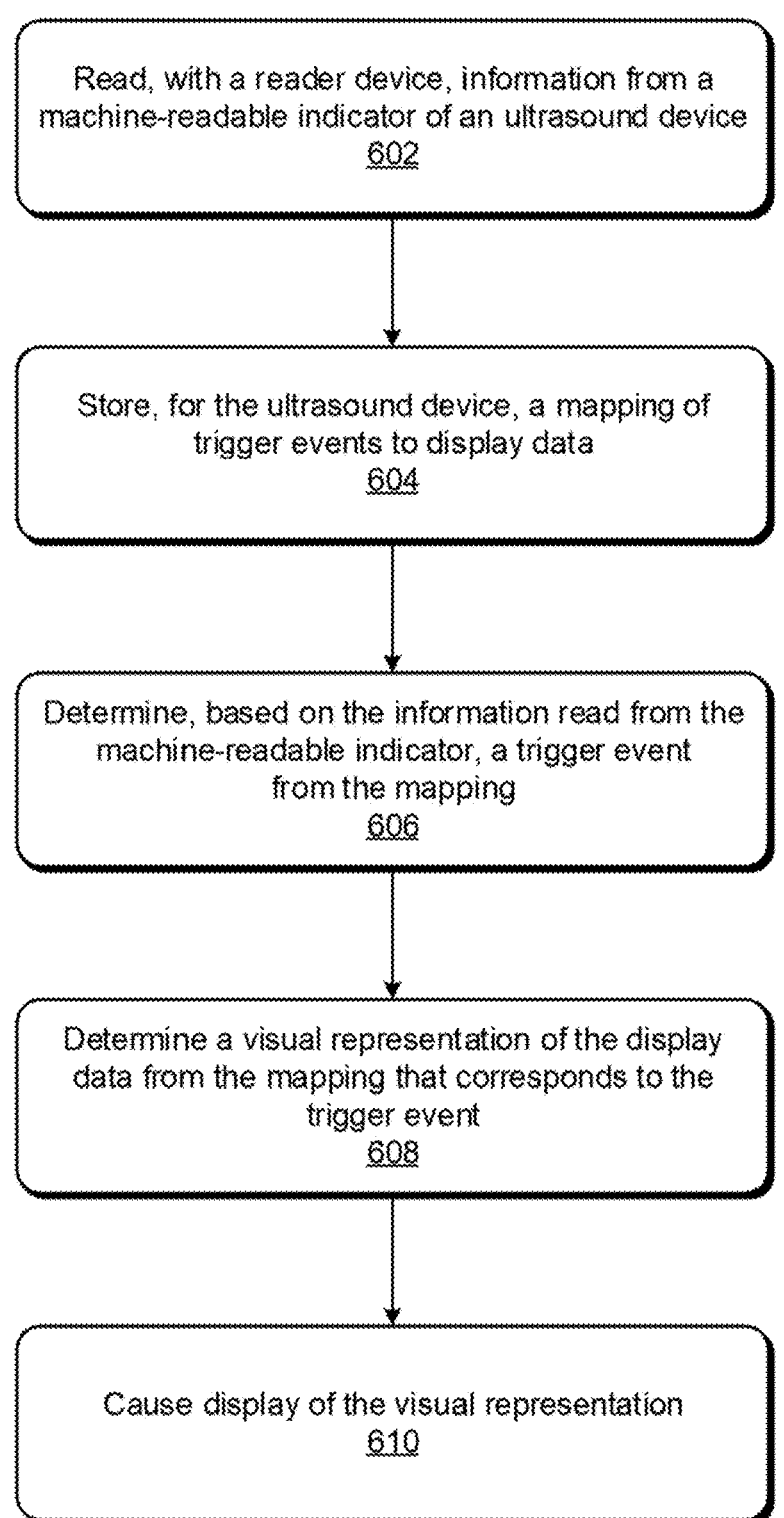

Read, with a reader device, information from a
machine-readable indicator of an ultrasound device
602

Store, for the ultrasound device, a mapping of
trigger events to display data
604

Determine, based on the information read from the
machine-readable indicator, a trigger event
from the mapping
606

Determine a visual representation of the display
data from the mapping that corresponds to the
trigger event
608

Cause display of the visual representation
610

Figure 7:
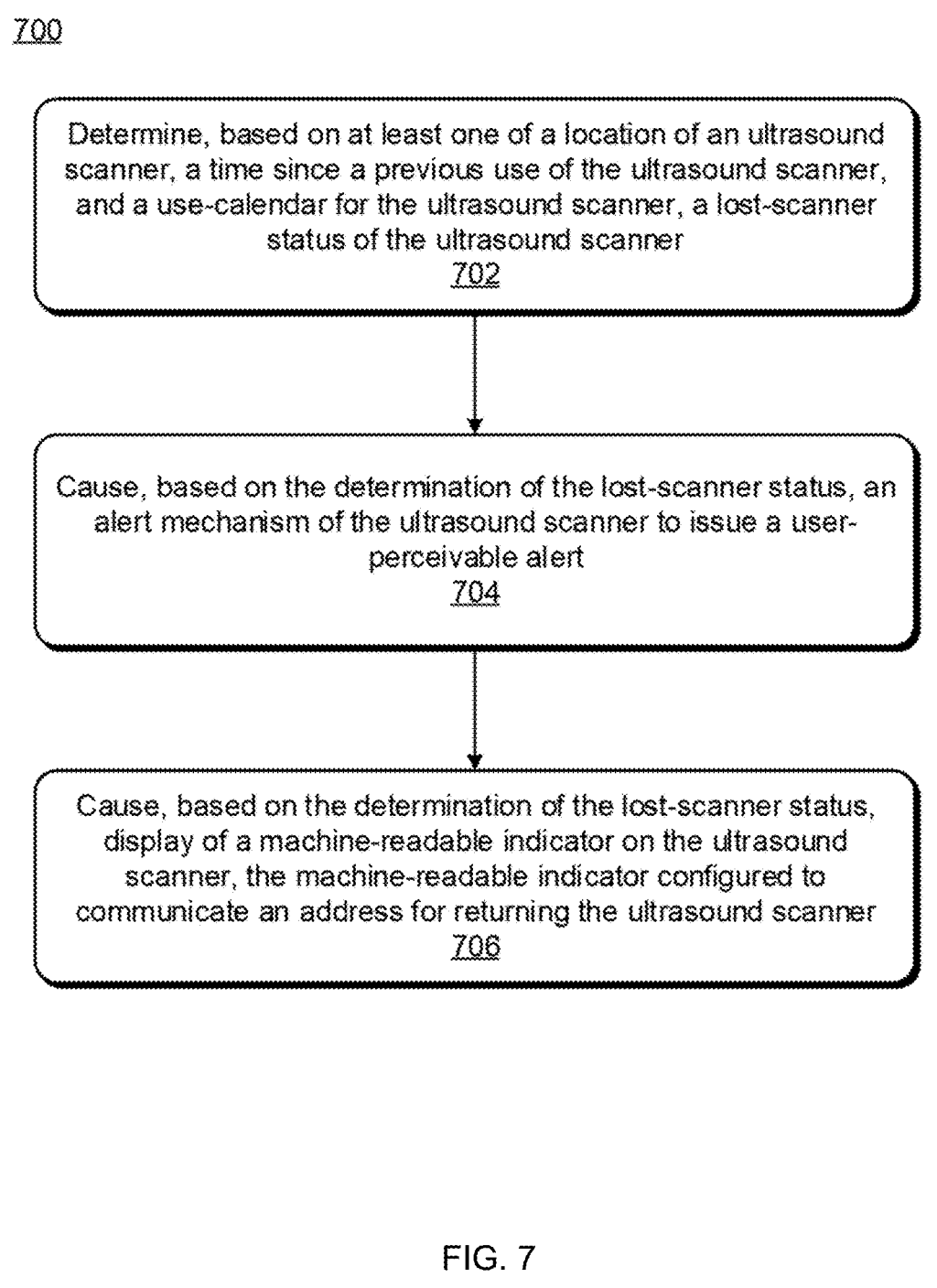

Determine, based on at least one of a location of an ultrasound scanner, a time since a previous use of the ultrasound scanner, and a use-calendar for the ultrasound scanner, a lost-scanner status of the ultrasound scanner
702

Cause, based on the determination of the lost-scanner status, an alert mechanism of the ultrasound scanner to issue a user-perceivable alert
704

Cause, based on the determination of the lost-scanner status, display of a machine-readable indicator on the ultrasound scanner, the machine-readable indicator configured to communicate an address for returning the ultrasound scanner
706

Read, with a reader device, information from
machine-readable indicators of ultrasound devices
<u>802</u>

Display, based on the information, a visual
representation that recommends one of the
ultrasound devices for an ultrasound examination
<u>804</u>

DISPLAYING DATA BASED ON MACHINE-READING OF AN ULTRASOUND DEVICE

Embodiments disclosed herein relate to ultrasound systems. More specifically, embodiments disclosed herein relate to displaying data based on machine-reading of an ultrasound device.

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Ultrasound systems can include ultrasound devices, such as an ultrasound scanner (also referred to as an ultrasound probe) that can include a transducer array implemented to transmit the ultrasound and receive the ultrasound echo signals, and a display device implemented to display an ultrasound image generated from the received ultrasound echo signals. The display device can be coupled to the ultrasound scanner via a cable and/or a wireless communication link.

Some ultrasound devices can include labels affixed to their surface, and these labels can include information about the ultrasound devices. However, the labels are often damaged or unreadable due to use and cleaning of the ultrasound devices, which can prevent a user from accessing the information on the label. Further, to repair a damaged label on an ultrasound device, the ultrasound device may need to be returned to the manufacturer for service, which is inconvenient, time consuming, and costly for the owner of the ultrasound device.

Some labels on ultrasound devices contain a reference to a location (such as a uniform resource locator (URL) or remote management service), that contains the information about the ultrasound devices, rather than the label itself including the information. However, in some cases, access to the location referenced by the label can be delayed, or simply not feasible, such as at point-of-care locations, including a triage center, a battlefield, a crowded emergency room, and the like. If the information is necessary for the user to operate the ultrasound device, such as operation instructions or access/authentication codes, the user may not be able to properly operate the ultrasound device.

Accordingly, conventional ultrasound systems can inhibit or prevent a user from accessing information about an ultrasound device, which can delay or prevent the user from properly operating the ultrasound device. Hence, patients may not receive the best care possible with conventional ultrasound systems.

SUMMARY

Systems and methods for displaying data based on machine-reading of an ultrasound device are described. In some embodiments, an ultrasound system includes an ultrasound device having a machine-readable indicator. The ultrasound system also includes a reader device configured to read information from the machine-readable indicator and a display device configured to display device information about the ultrasound device based on the information read from the machine-readable indicator.

In some other embodiments, an ultrasound system includes an ultrasound device having a machine-readable indicator and a reader device configured to read information from the machine-readable indicator. The ultrasound system also includes a memory storing, for the ultrasound device, a mapping of trigger events to display data. The ultrasound system includes a processor system configured to determine, based on the information read from the machine-readable indicator, a trigger event from the mapping, determine a visual representation of the display data from the mapping that corresponds to the trigger event, and cause display of the visual representation.

In still some other embodiments, an ultrasound scanner includes a machine-readable indicator displayable on an external surface of the ultrasound scanner and an alert mechanism configured to issue a user-perceivable alert. The ultrasound scanner also includes a processor system configured to determine, based on at least one of a location of the ultrasound scanner, a time since a previous use of the ultrasound scanner, and a use-calendar for the ultrasound scanner, a lost-scanner status of the ultrasound scanner, cause, based on the determination of the lost-scanner status, the alert mechanism to issue the user-perceivable alert; and cause, based on the determination of the lost-scanner status, display of the machine-readable indicator, where the machine-readable indicator is configured to communicate an address for returning the ultrasound scanner.

In some embodiments, an ultrasound system includes one or more ultrasound devices and a reader device that is configured to read information from machine-readable indicators of ultrasound devices. The ultrasound system also includes a processing system that is configured to display, based on the information, a visual representation that recommends one of the ultrasound devices for an ultrasound examination.

In some embodiments, a method implemented by a computing device includes exposing, via an ultrasound device, a machine-readable indicator and reading, with a reader device, information from the machine-readable indicator. The method also includes displaying, with a display device, device information about the ultrasound device based on the information read from the machine-readable indicator.

In some other embodiments, a method implemented by a computing device includes reading, with a reader device, information from a machine-readable indicator of an ultrasound device. The method also includes storing, for the ultrasound device, a mapping of trigger events to display data and determining, based on the information read from the machine-readable indicator, a trigger event from the mapping. The method further includes determining a visual representation of the display data from the mapping that corresponds to the trigger event and causing display of the visual representation.

In yet some other embodiments, a method implemented by a computing device includes determining, based on at least one of a location of an ultrasound scanner, a time since a previous use of the ultrasound scanner, and a use-calendar for the ultrasound scanner, a lost-scanner status of the ultrasound scanner. The method also includes causing, based on the determination of the lost-scanner status, an alert mechanism of the ultrasound scanner to issue a user-perceivable alert and causing, based on the determination of the lost-scanner status, display of a machine-readable indicator on the ultrasound scanner. The machine-readable indicator is configured to communicate an address for returning the ultrasound scanner.

In still some other embodiments, a method implemented by a computing device includes reading, with a reader device, information from machine-readable indicators of ultrasound devices. The method also includes displaying, based on the information, a visual representation that recommends one of the ultrasound devices for an ultrasound examination.

Other systems, devices, and methods for displaying data based on machine-reading of an ultrasound device are also described.

BRIEF DESCRIPTION OF THE DRAWINGS

The appended drawings illustrate examples and are, therefore, exemplary embodiments and not considered to be limiting in scope.

FIG. 2B is a view that illustrates using an ultrasound device display information to trigger different augmented interactions according to some embodiments.

FIG. 5 illustrates a method that can be performed by an ultrasound system in accordance with some embodiments.

FIG. 6 illustrates a method that can be performed by an ultrasound system in accordance with some embodiments.

FIG. 7 illustrates a method that can be performed by an ultrasound device according to some embodiments.

FIG. 8 illustrates a method that can be performed by an ultrasound system according to some embodiments.

DETAILED DESCRIPTION

Figure 1:
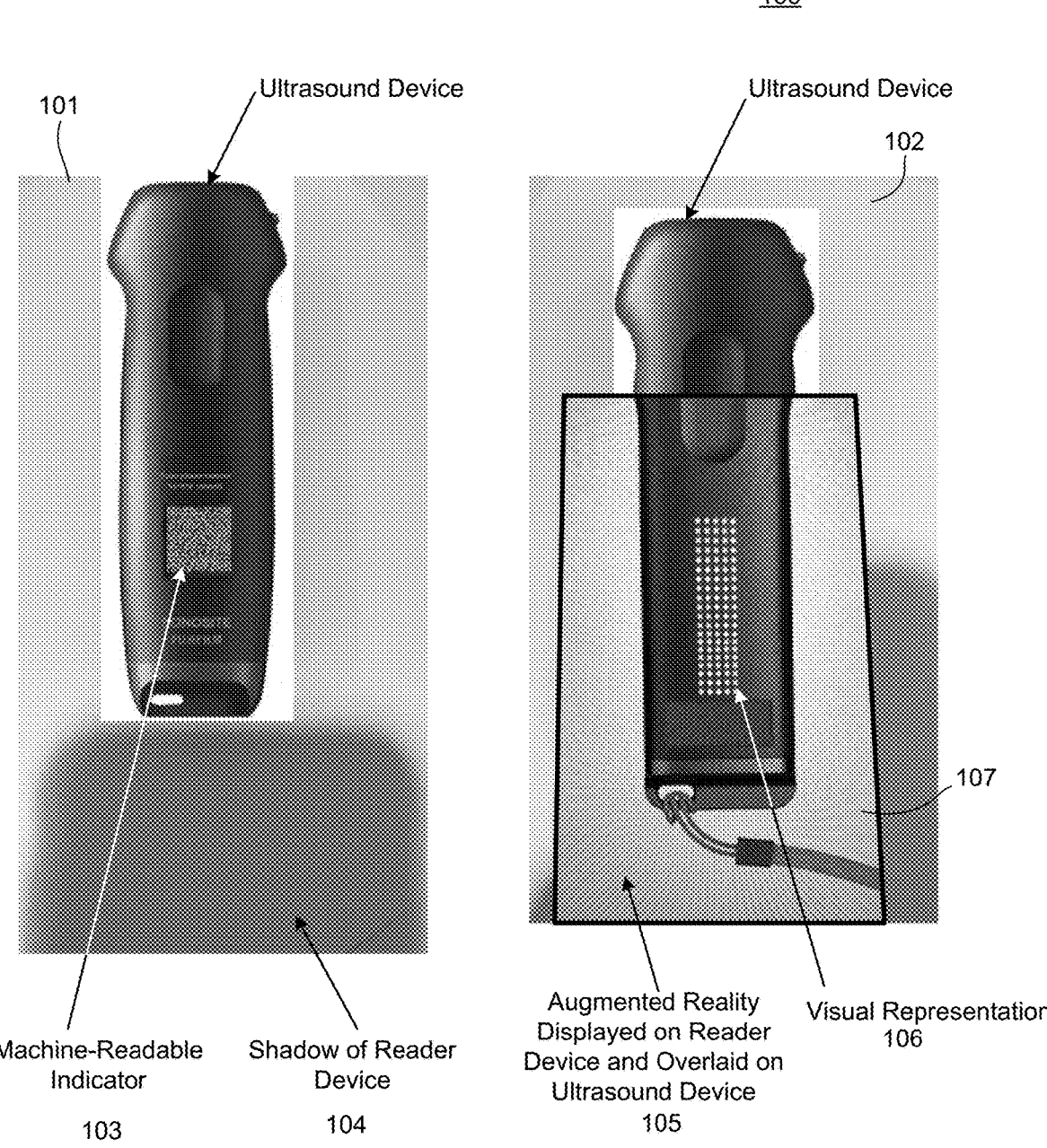
FIG. 1 is a view illustrating the reading a machine-readable indicator displayed on an ultrasound scanner, and displaying a visual representation in an augmented reality (AR) environment based on the information of machine-readable indicator according to some embodiments.

In the following description, numerous details are set forth to provide a more thorough explanation of embodiments of the present disclosure. It will be apparent, however, to one skilled in the art, that embodiments of the present disclosure may be practiced without these specific details. In other instances, well-known structures and devices are shown in block diagram form, rather than in detail, in order to avoid obscuring embodiments of the present disclosure.

Conventional ultrasound systems can inhibit or prevent a user from accessing information about an ultrasound device of the ultrasound system. This lack of access can delay or prevent the user from properly operating the ultrasound device. Hence, patients may not receive the best care possible with conventional ultrasound systems. Accordingly, systems, devices, and techniques are disclosed herein for reading a machine-readable indicator displayed on or by an ultrasound device, and displaying, based on information determined from the machine-readable indicator, a visual representation that can be related to the ultrasound device. The systems, devices, and techniques are disclosed herein for showing data (e.g., battery power, or other data) related to an ultrasound device (e.g., a scanner, a mobile system). The systems, devices, and techniques are disclosed herein for showing dynamic, customizable information that would be useful to the device user, manager, or owner without using a device management portal (e.g., dashboards).

Terms

"Augmented reality environment" refers to an immersive imaging environment that includes a synthetic object (e.g., a computer-generated image or icon) that is superimposed on a real-world view. Hence, an augmented reality environment provides a composite view of synthetic and real-world objects.

"Display data" refers to data or datum that can be stored in one or more memories and be used to generate a visual representation that can be displayed (e.g., in an augmented reality environment) and that represents the display data, or includes information of the display data. An example of display data is text, e.g., stored in an ASCII file. A visual representation generated for this display data can include an image or icon that includes the text, in any suitable font type or size for the display device on which the visual representation is displayed. Another example of display data is a vector graphics description of an icon, and an example of a visual representation for this display data is a renderable icon generated according to the vector graphics description. Another example of display data is a file with multiple pages, such as, for example, but not limited to, a PDF file. A visual representation for this display data can include a single page of the file. In some embodiments, display data and a visual representation of the display data are the same thing, such as an image file (e.g., a jpg image).

"Display device" refers to any suitable device that can implemented to display an image in a conventional environment and/or an immersive environment (e.g., an augmented reality environment). Examples of display devices include a smartphone, tablet, and ultrasound machine. In some embodiments, a display device includes an ultrasound scanner (e.g., the ultrasound scanner can include a display interface). In some embodiments, a display device includes a reader device. For instance, the reader device can include a display screen.

"Machine-readable indicator" refers to an indicator that can be read by a machine, such as a reader device or computer, and can be placed on or in an ultrasound device. Machine-readable indicators can include displayable indicators that are visible and encoded with information, such as, for example, a quick response (QR) code or a bar code. Other examples of machine-readable indicators that are visible include displays of images, icons, patterns, etc. In some examples, a machine-readable indicator can depict information that is perceivable by a human, such as text or a number. In some embodiments, machine-readable indicators include light sources that emit light (e.g., light encoded with information) that is outside the visible spectrum (e.g., light having a wavelength outside of the range of 380 nanometers to 740 nanometers). In some embodiments, machine-readable indicators include speakers and/or transducers configured to emit sounds that are encoded to communicate information, such as discrete tones and chirps.

"Mapping" refers to any suitable data structure that associates trigger events with display data. For example, a trigger event can correspond to the display of a character on an ultrasound device, and the mapping can store display data for generating an image when the trigger event is detected on the ultrasound device. Hence, when a reader device reads the character on the ultrasound device, the display data mapped to that character can be retrieved from the mapping, and an image can be generated from the display data and exposed to a user. Different mappings can be stored for different ultrasound devices (e.g., device classes, device models, device states, etc.), different users, different departments in a care facility, etc., allowing for flexibility when the ultrasound device is used in accordance with embodiments of the present disclosure.

"Reader device" refers to any suitable device configured to read information of a machine-readable indicator, such as a device with a QR or barcode scanner/reader, or suitable imaging device. A reader device can also include a device configured to capture a physical feature indicator of the ultrasound device, such as its shape, size, or physical configuration.

"Trigger event" refers to the exposure of information via a machine-readable indicator of an ultrasound device. An example of a trigger event includes the display of a QR code on a display screen of an ultrasound device. The trigger event is detected when the information is read by a reader device.

"Ultrasound device" refers to any suitable component of an ultrasound system. Examples of ultrasound devices include an ultrasound machine, ultrasound scanner, ultrasound cart, charging station, display device, a transducer cable, a transducer cable holder, a docking station for an ultrasound machine, a scanner station configured to hold one or more ultrasound scanners, a needle guide, a battery for a wireless ultrasound scanner, a battery for an ultrasound machine, and the like.

"Visual representation" refers to an object that can be determined or generated based on display data stored in a mapping, and displayed for user consumption. Examples of visual representations include images, icons, animation sequences, video tutorials, text, etc.

Example Embodiments

Systems, devices, and techniques are disclosed herein for reading a machine-readable indicator displayed on or by an ultrasound device, and displaying, based on information determined from the machine-readable indicator, a visual representation that can be related to the ultrasound device. The visual representation can be displayed in an augmented reality (AR) environment that includes the ultrasound device (e.g., the visual representation can include an icon that is overlaid on top of the ultrasound device in the AR environment). The machine-readable indicator can be displayed on a display screen of the ultrasound device, and include a quick response (QR) code, a bar code, an animation sequence, a pattern, an image, and the like. For various ultrasound devices, the ultrasound system can maintain mappings of different machine-readable indicators to different display data that describes the visual representations.

The ultrasound system can maintain different mappings for different device classes (e.g., a set of mappings for different ultrasound scanners and a different set of mappings for ultrasound machines), as well as mappings for different device states (e.g., a first mapping for an ultrasound scanner in a device state corresponding to in-use, and a second mapping for an ultrasound scanner in a device state corresponding to cleaning). Accordingly, the ultrasound system can improve the workflow of the user of an ultrasound device in numerous ways, including to guide the user through an ultrasound protocol, assisting the user in populating a medical worksheet, providing ultrasound device data to the user, recommending an ultrasound device to a user, etc.

FIG. 1 is a view 100 illustrating the reading of a machine-readable indicator displayed on an ultrasound scanner, and displaying a visual representation in an augmented reality (AR) environment based on the information of machine-readable indicator according to some embodiments. FIG. 1 depicts two image panels, an image panel 101 and an image panel 102. The image panel 101 depicts an ultrasound scanner as an example of an ultrasound device. The ultrasound scanner displays a machine-readable indicator 103. In this example, the machine-readable indicator includes a quick response (QR) code that is displayed on a surface of the ultrasound scanner. For instance, the ultrasound scanner can include a display interface to display the machine-readable indicator, as described in U.S. patent application Ser. No. 18/045,362 entitled Ultrasound Scanner with Display Interface filed on Oct. 10, 2022, the disclosure of which is incorporated herein by reference in its entirety. The image panel 101 also depicts a shadow 104 of a reader device as the reader device is being moved over the ultrasound scanner, so that the reader device can read information contained in the machine-readable indicator. For example, the reader device can include a smart-phone configured with an application and camera implemented to read the QR code.

The image panel 102 depicts the ultrasound device (in this example, an ultrasound scanner) overlaid with an augmented reality environment 105 depicted on a reader device 107. For instance, as the reader device 107 is moved over the ultrasound scanner to read the machine-readable indicator, and once the information of the machine-readable indicator is read by the reader device, the reader device 107 generates and displays the augmented reality environment 105. In this example, the augmented reality environment displays a visual representation 106 that is determined by the ultrasound system based on the information read from the machine-readable indicator. In FIG. 1, the visual representation 106 includes a bar graph that depicts a battery level of the ultrasound scanner. The ultrasound system can maintain a mapping of trigger events (e.g., display of machine-readable indicators) to display data used to generate the visual representations, as described below in more detail.

Figure 2A:
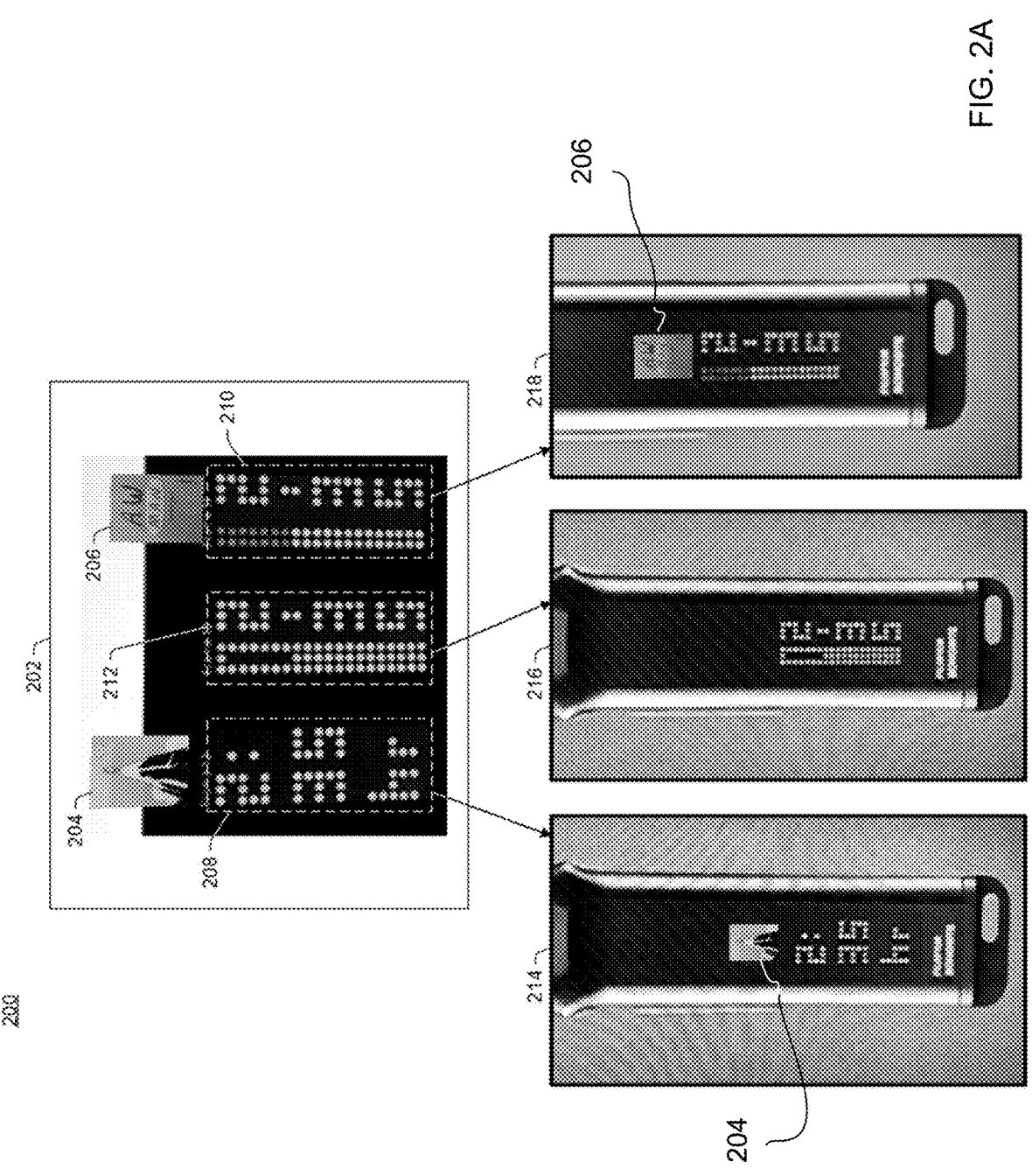
FIG. 2A is a view that illustrates different machine-readable indicators on an ultrasound scanner to trigger the display of different visual representations in an augmented reality environment according to some embodiments.

FIG. 2A is a view 200 that illustrates different machine-readable indicators on an ultrasound scanner to trigger the display of different visual representations in an augmented reality environment according to some embodiments. FIG. 2A generally depicts how the display of different machine-readable indicators on an ultrasound scanner serves as trigger events for the display of different visual representations in an augmented reality environment. FIG. 2A includes information of a mapping 202 that can be stored in a memory of the ultrasound system. The mapping can associate different trigger events (e.g., the display of different machine-readable indicators) with display data for different visual representations. For example, in FIG. 2A the mapping 202 depicts a first visual representation 204 and a second visual representation 206. The first visual representation 204 is generated from display data that is mapped to the trigger event 208 (e.g., the display of "2:35 hr" by a machine-readable indicator). The second visual representation 206 is generated from display data that is mapped to the trigger event 210 (e.g., the display by a machine-readable indicator of "2:35" with a specific dot pattern of a bar graph). The trigger event 212 (e.g., the display by a machine-readable indicator of "2:35" with a different dot pattern of a bar graph than that of the trigger event 210) is not mapped to display data for a visual representation.

FIG. 2A also depicts displays 214, 216, and 218 than can be generated by the ultrasound system responsive to a reader device reading the trigger events 208, 212, and 210, respectively, on an ultrasound device, such as an ultrasound scanner. The displays 214, 216, and 218 can be displayed on any suitable component of the ultrasound system, including the reader device, an ultrasound machine, a display device, etc. When the ultrasound device displays the trigger event 208 via a machine-readable indicator and the reader device detects the display of the trigger event 208, the ultrasound system causes the display 214 to depict in an augmented reality environment the visual representation 204, according to the mapping 202.

When the ultrasound device displays the trigger event 210 via a machine-readable indicator and the reader device detects the display of the trigger event 210, the ultrasound system causes the display 218 to depict in an augmented reality environment the visual representation 206, according to the mapping 202. However, the mapping 202 does not include display data for a visual representation that is associated with the trigger event 212. Hence, when this trigger event 212 is detected by the ultrasound system, no visual representation is displayed in an augmented reality environment, as depicted by the display 216.

FIG. 2B is a view 220 that illustrates using an ultrasound device to display information to trigger different augmented interactions according to some embodiments. As shown in FIG. 2B, an ultrasound device displays a machine-readable indicator 221 that indicates that a scan time remaining is 95 mins. When a reader device detects the display of the machine-readable indicator 221, the ultrasound system causes the display of the reader device to display the visual representation indicating a device status 223. The device status 223 includes information indicating the device connection, remaining scan time, device status, battery status, device owner, and a visual representation 225 for a user to perform one or more additional actions, e.g., request a new scanner, as shown in FIG. 2B.

As shown in FIG. 2B, an ultrasound device displays a machine-readable indicator 222 that includes a QR code. When a reader device detects the display of the machine-readable indicator 222, the ultrasound system causes the display of the reader device to depict the visual representation indicating a device regulatory information 224. The regulatory information 224 includes information indicating the product name, a model number, and other regulatory information, as shown in FIG. 2B.

Figure 2C:
FIG. 2C is a view that illustrates displaying in an AR environment data from one or more ultrasound devices according to some embodiments.

FIG. 2C is a view 230 that illustrates displaying in an AR environment data from one or more ultrasound devices according to some embodiments. As shown in FIG. 2C, a scanner station 235 is configured to hold one or more ultrasound scanners, e.g., ultrasound scanners 231, 232, 233 and 234. Each of the ultrasound scanners displays a machine-readable indicator, as shown in FIG. 2C. A reader device is configured to read the information from machine-readable indicators while the ultrasound scanners are housed by the scanner station 235. The reader device is configured to display the device information 236, such as on a display of the reader device and/or in an AR environment. In some embodiments, the machine-readable indicator on each of the ultrasound scanners indicates a remaining scan time. In some embodiments, the device information 236 includes a recommendation of one of the ultrasound scanners for an ultrasound examination based on the remaining scan time.

The trigger events depicted via the machine-readable indicators can include any suitable event. Examples include the display of a scan time remaining, a battery power level, a QR code, a bar code, an animation sequence, a pattern, an icon, an image, a numerical value, an alphabet character, or combinations thereof. Further, the machine-readable indicators are not limited to the display of visible information to depict a trigger event. In some embodiments, the machine-readable indicators include light sources that depict a trigger event with light outside the visible spectrum (e.g., light having a wavelength outside of the range of 380 nanometers (nm) to 740 nm). Although this light may not be perceivable by a human, it can be read by a suitable reader device (e.g., a reader device equipped with an infrared (IR) camera).

Additionally or alternatively, the machine-readable indicators can depict a trigger event via a sound. For instance, the machine-readable indicators can include speakers and/or transducers configured to emit a sound. Different frequencies can represent different trigger events. For instance, a first frequency can represent a first trigger event, and a second frequency can represent a second trigger event. In some embodiments, the trigger events can be represented by multiple frequencies. For instance, a chirp made up of increasing frequencies can depict one trigger event, and a chirp made up of decreasing frequencies can represent another trigger event. The sound can be perceivable by a human (e.g., in the range of 20 Hz to 20 KHz). In some other embodiments, the sound includes ultrasound that is above the audible spectrum perceivable by a human. Accordingly, the reader device can include a suitable microphone and/or transducer configured to read (e.g., detect) the audible trigger event.

In some embodiments, the machine-readable indicators can depict a trigger event by causing the ultrasound device to vibrate. The frequency and/or amplitude of vibration can be encoded to represent the trigger event. For instance, a first vibration frequency can depict one trigger event, and a second vibration frequency can depict another trigger event. The reader device can read the frequency and/or amplitude of vibration with any suitable sensor, such as a microphone, vibration sensor, etc. An example of a vibration sensor includes a laser capable of detecting mechanical movement of an ultrasound device caused by vibration.

In some embodiments, the machine-readable indicators and/or trigger events are dynamic, in that they can be updated, such as when an ultrasound device has software that is updated via a remote management and monitoring application. The mapping of trigger events depicted by the machine-readable indicators to display data for visual representations can also be dynamically updated and maintained by a storage memory of the ultrasound system. Additionally or alternatively, machine-readable indicators and/or trigger events can be static, and thus not dynamically updateable. For instance, a machine-readable indicator can include dimples molded into the surface of an ultrasound device in a pattern. When the pattern of dimples is read by a reader device (e.g., imaged with a camera of the reader device), the reader device can display device information for the ultrasound device. Examples of device information include a model number, software version number, an identification of another device that is paired to the ultrasound device, a cleaning status of the ultrasound device, and the like. In some embodiments, the mapping can be dynamically updated to adjust what visual representation is associated with the reading of a static machine-readable indicator. For instance, for a first version of the mapping, the reading of a pattern of dimples can be mapped to display data for a visual representation that depicts a model number and software version for the ultrasound device. An updated version of the mapping can add a device owner to the list of device information that is mapped to the reading of the pattern of dimples.

The machine-readable indicators can depict the occurrence of any suitable trigger event. In some embodiments, an ultrasound device includes a temperature sensor (e.g., a thermometer). When the temperature of the ultrasound device exceeds a threshold temperature, the machine-readable indicator can indicate the excess temperature as a trigger event. The reader device can read the machine-readable indicator and display a visual representation to alert a user to obtain a different ultrasound device, or adjust the ultrasound device to reduce the temperature.

In some embodiments, the trigger event is determined based on the orientation of the ultrasound device and/or a pressure applied to the ultrasound device. For instance, when an ultrasound scanner is oriented substantially vertically and/or with its lens pressing against a patient, the machine-readable indicator can depict that the ultrasound scanner is in use, as opposed to being charged or cleaned. When pressure is applied to a distal end of the ultrasound scanner (e.g., the end of the ultrasound scanner opposing the lens), the ultrasound scanner can determine that the weight of the scanner itself is causing the pressure and that the device is being stored, e.g., in a scanner station configured to house ultrasound scanners. Hence, the machine-readable indicator can depict that the ultrasound scanner is in a storage state. To determine pressure applied to the ultrasound device, the ultrasound device can include any suitable sensor, as described in U.S. patent application Ser. No. 18/045,477 entitled Configuring Ultrasound Systems based on Scanner Grip filed on Oct. 11, 2022, the disclosure of which is incorporated herein by reference in its entirety.

In some embodiments, the machine-readable indicator is not only configured to be readable by a machine (e.g., a reader device), but also can be read by a human. In some embodiments, a machine-readable indicator that is human-readable can be an advantage, such as when the information depicted by the machine-readable indicator is not sensitive information (e.g., is publicly available data). However, for sensitive data, e.g., patient data, a machine-readable indicator that is not human-readable, such as a QR code, can be advantageous, since it hides the sensitive data from users who do not have a suitable reader device, or do not have a suitable authentication level to access the sensitive information via a reader device. Hence, in some embodiments, a user may need to be authenticated to the ultrasound system to access the sensitive information of the machine-readable indicator via the reader device.

The ultrasound system can use a user status, such as an authentication status, authorization status, clinical status (e.g., physician vs. A nurse), level of accreditation, level of experience (e.g., years of experience), job title, etc., to determine what visual representation is exposed to a user. For example, for an unauthorized or unauthenticated user, a trigger event depicted via a machine-readable indicator can cause the ultrasound system to expose less sensitive information to the unauthorized/unauthenticated user, such as a user manual for an ultrasound device. However, for an authorized or authenticated user, the same trigger event depicted via the machine-readable indicator can cause the ultrasound system to expose more sensitive information to the authorized/authenticated user, such as a medical worksheet.

Further, the visual representations can include any suitable visual representation that can assist a user in performing a procedure. Examples of visual representations include images, icons, animation sequences, video tutorials, and text. Other examples include representations of medical worksheets, and representations of user manuals (e.g., a user manual for an ultrasound device that depicts a trigger event with a machine-readable indicator). Still other examples assist a user through a workflow, and can include a representation of a step in an ultrasound protocol, and a representation such as an arrow that directs a user to an ultrasound device to locate the ultrasound device (e.g., a display device or ultrasound machine that is paired with an ultrasound scanner). Yet some other embodiments include a representation of a cleaning status, such as a time since last cleaning of the ultrasound device, a representation of other devices connected to (wired or wirelessly) the ultrasound device, a representation of a previous user of the ultrasound device, and a representation that indicates suitable uses for the ultrasound device, such as anatomies that are well suited for imaging with an ultrasound scanner. In one example, the representation indicates a patient status, such as by identifying a patient who is to be examined by a user of the ultrasound device and a location (e.g., hospital room number or department identifier) where the patient is located. In some embodiments, the representation indicates an anatomy, and can be overlaid on the patient to indicate the position of the anatomy on the patient.

The visual representation is not limited to display device data for an ultrasound device. In some embodiments, the visual representation indicates information related to the context of the environment in which an ultrasound device is located. For instance, the visual representation can indicate medical devices that are in proximity to the ultrasound device, such as in the same room. In some other embodiments, the visual representation indicates a medical implant in a patient, such as a pacemaker, stent, or cardioverter-defibrillator. Additionally or alternatively, the visual representation can indicate the presence of other electronic equipment that is in proximity to the ultrasound device that may emit interference, such as an RFID emitter and/or reader.

In some embodiments, the ultrasound system maintains a plurality of mappings of trigger events to display data for visual representations. For example, a first set of mappings can be maintained for a first device class of ultrasound devices, such as a mapping for ultrasound scanners, and a second set of mappings can be maintained for a second device class of ultrasound devices, such as a mapping for ultrasound machines with clinical displays. In some other embodiments, a set of mappings is maintained for a device class of ultrasound devices of a first model number or numbers, such as a mapping for ultrasound scanners with model numbers within a certain range (e.g., ultrasound scanners with model numbers 1-6). Another set of mappings can be maintained for another device class of ultrasound devices of a second model number or numbers, such as a mapping for ultrasound scanners with model numbers within another range (e.g., ultrasound scanners with model numbers 7-9).

Accordingly, the ultrasound system can determine a device class for an ultrasound device, and based on the device class, access a suitable mapping for the device. The ultrasound system can then read information from a machine-readable indicator for the ultrasound device, and determine, based on the information, that a trigger event has occurred. The ultrasound system can match display data for a visual representation to the trigger event from the mapping it determined from the device class, and then display the visual representation. The display of the visual representation can be in an AR environment overlaid on the ultrasound device, as depicted above in FIG. 1. Additionally or alternatively, the display of the visual representation can omit an AR environment. For example, a reader device can display on a touchscreen of the reader device a visual representation generated from display data of a mapping, and the touchscreen need not be AR-enabled.

The ultrasound system can determine a device class for an ultrasound device in any suitable way. In some embodiments, the reader device captures a physical feature indication of the ultrasound device. In some embodiments, the reader device includes a camera to image the ultrasound device and capture the physical feature indication based on the imaging. Examples of a physical feature indication include a shape of the ultrasound device, a size of the ultrasound device, a layout configuration of the ultrasound device, a number of buttons, knobs, or sliders on the ultrasound device, a location of the ultrasound device relative to another device, and combinations thereof. Based on the physical feature indication for an ultrasound device, the ultrasound system can determine a device class for the ultrasound device. For instance, the shape of the ultrasound device can be used to distinguish between ultrasound scanners and ultrasound machines, from among different models of ultrasound scanners and/or ultrasound machines, etc.

Figure 3:
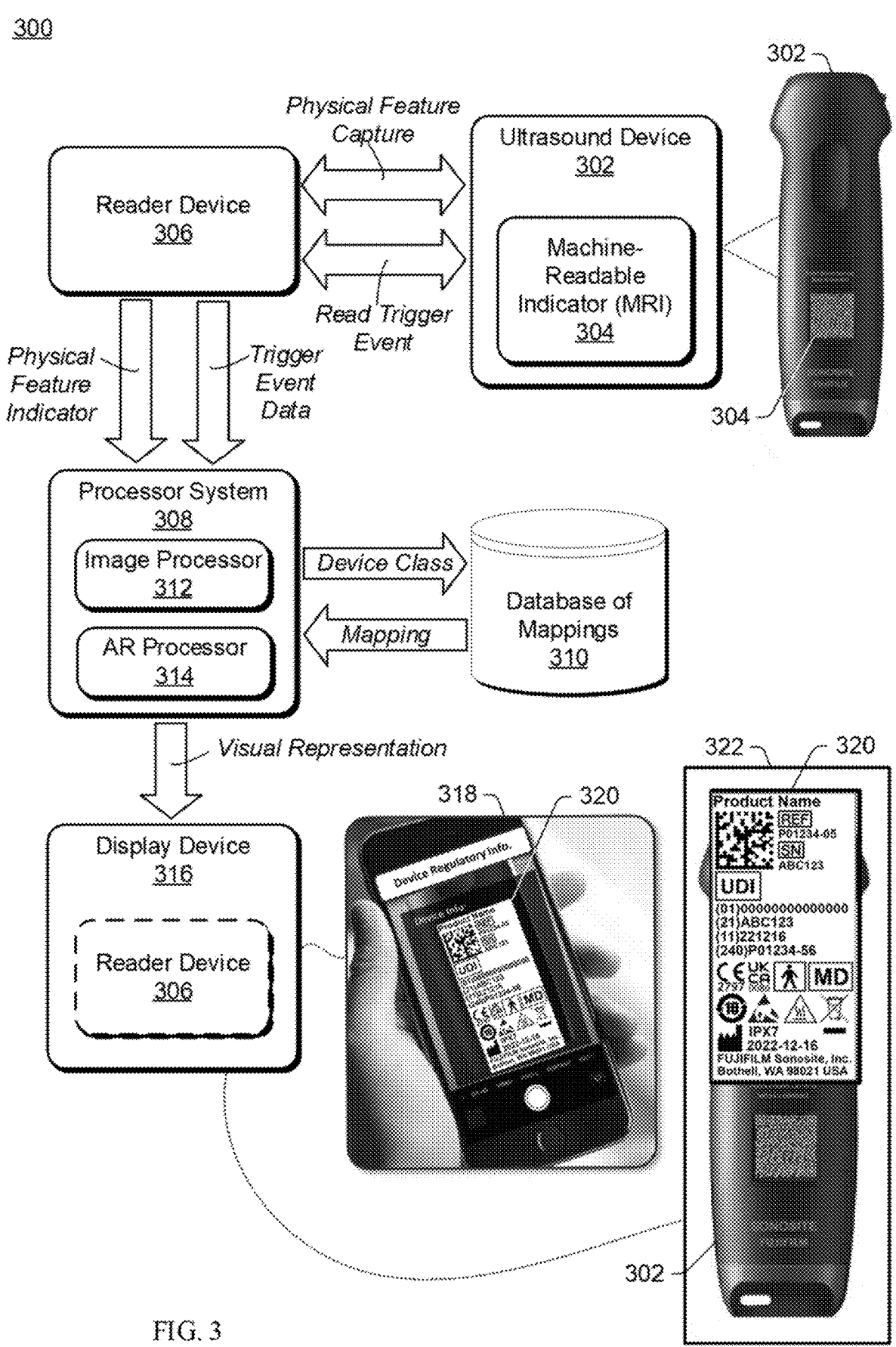
FIG. 3 illustrates an ultrasound system in accordance with some embodiments.

FIG. 3 illustrates an ultrasound system 300 in accordance with some embodiments. The ultrasound system 300 includes an ultrasound device 302, which can include any suitable component of an ultrasound system, such as an ultrasound machine, ultrasound scanner, ultrasound cart, charging station, display device, and the like. As an example, the ultrasound device 302 in FIG. 3 is illustrated as an ultrasound scanner. The ultrasound device 302 includes a machine-readable indicator 304, such as a QR code, a bar code, an animation sequence, a pattern, an icon, an image, a numerical value, an alphabet character, and the like. The machine-readable indicator 304 can be displayed via a display screen, one or more light sources, a physical property on an external surface of the ultrasound device 302 (e.g., dimples or ridges formed in a pattern), or indicated via an audio source, as previously described.

The ultrasound system 300 also includes a reader device 306 configured to read information contained in, or exposed by, the machine-readable indicator 304. The reader device 306 can also determine a physical feature indicator of the ultrasound device 302. For instance, the reader device 306 can capture an image of the ultrasound device 302 and determine the physical feature indicator that describes a shape of the ultrasound device 302. The reader device 306 provides the physical feature indicator of the ultrasound device 302 to a processor system 308 of the ultrasound system 300.

The processor system 308 can include any suitable type and number of processors. In some embodiments, the processor system 308 includes one or more processors. In the example illustrated in FIG. 3, the processor system 308 includes an image processor 312 and an augmented reality (AR) processor 314. The image processor 312 can be configured to generate graphics data for images that can be displayed on a screen of a display device, such as on a touchscreen. The AR processor 314 can be configured to generate graphics data for images that can be displayed in an augmented reality environment by a display device. In some embodiments, the AR processor 314 generates icons of an AR object and overlay the icons on an image generated in accordance with the graphics data generated by the image processor 312. Hence, the image processor 312 and the AR processor 314 can work in conjunction with one another to generate graphics data for an image displayed by a display device. In some embodiments the graphics data includes a visual representation that is generated by the processor system 308 based on image data stored in a mapping of the database of mappings 310 (described below in more detail). The graphics data can be displayed in an augmented reality environment or in a standard (e.g., non-augmented reality) imaging environment.

The processor system 308 receives the physical feature indicator from the reader device 306 and determines a device class based on the physical feature indicator. In one example, the processor system 308 implements one or more neural networks configured to process the physical feature indicator and generates a label that includes the device class. Additionally or alternatively, the processor system 308 can include a table that includes device classes and physical feature indicators associated with the device classes. The processor system 308 can then determine the device class by matching the physical feature indicator from the reader device 306 to a physical feature indicator in the table. For instance, the processor system 308 can match a shape described by the physical feature indicators, or any suitable property of the physical feature indicators.

The ultrasound system 300 also includes, or has access to, a database of mappings 310, which includes mappings of trigger events to display data for visual representations. The database of mappings 310 can include various mappings for different device classes, and based on the device class determined by the processor system 308, the database of mappings 310 provides a mapping to the processor system 308.

The reader device 306 is also implemented to determine a trigger event of the ultrasound device 302 by reading information contained in, or exposed by, the machine-readable indicator 304 of the ultrasound device 302. For instance, the reader device 306 can read a QR code displayed by the ultrasound device 302 and based on the reading, generate trigger event data that describes the information of the machine-readable indicator 304. The reader device 306 provides the trigger event data to the processor system 308.

The processor system 308 receives the trigger event data from the reader device 306 and using the mapping provided by the database of mappings 310, determines display data that is associated with the trigger event. Using one or more processors, e.g., the image processor 312 or the AR processor 314, the processor system 308 generates a visual representation of the display data to display to a user. For example, the display data provided from the mapping can include text associated with a trigger event. The processor system 308 can generate a visual representation that includes the text, and the visual representation can depend on the display format of the display device 316. Hence, the processor system 308 can also generate any suitable graphics data for the display device 316, such as graphics data needed to display the visual representation. The processor system 308 provides the visual representation and any suitable graphics data to the display device 316. The display device 316 can include any suitable display device. In one example, the display device 316 includes the reader device 306, so that the reader device 306 can display the visual representation associated with the trigger event.

Inset 318 illustrates an example of the display device 316, and includes a visual representation that includes device information 320 that is displayed on a touchscreen of a smartphone. The device information 320 includes information that describes the ultrasound device 302. In some embodiments, the smartphone and the reader device 306 are the same device. Inset 322 illustrates another example of the display device 316, and includes the visual representation including the device information 320 in an augmented reality environment. In some embodiments, the inset 322 overlays the device information 320 on top of an image of the ultrasound device 302 in an augmented reality environment.

The database of mappings 310 can maintain different mappings for different device classes as described above (e.g., a set of mappings for different ultrasound scanners and a different set of mappings for ultrasound machines), as well as different mappings for different device states. Examples of device states include a charging state (e.g., when the ultrasound device is being charged), a pairing state (e.g., when the device is in the process of being paired with another device, or is already paired), a transportation state (e.g., when the device is being moved), a cleaning sate (e.g., when the device is being cleaned), and an in-use state (e.g., when the device is being used in an ultrasound examination). Additionally or alternatively, the database of mappings 310 can maintain different mappings for different departments, such as a first mapping for a radiology department and a second mapping for an emergency department in a hospital.

Further, the database of mappings 310 can maintain different mappings for different users, and update a mapping for a user based on the user's history. For instance, novice users may need to be shown guided workflows via the visual representations displayed by the ultrasound system, but a more experienced user may not need to be shown the same visual representations as a novice user. In some embodiments, the visual representations for a novice user include to highlight a button that needs to be pressed in an examination. However, as that user learns and becomes a more skilled operator, the ultrasound system can update the mapping for that user so that the visual representation to highlight the button is no longer associated with a trigger event. The ultrasound system can determine the skill level for a user in any suitable way, such as, for example, based on a test score for the user, comparing the user against other users who are determined to be skilled, and the like.

An ultrasound system according to some embodiments of the present disclosure, such as the ultrasound system 300, is not limited to use in a care facility when caring for a patient. In some embodiments, the ultrasound system can be used by a manufacturer of the ultrasound device. For instance, suppose a care facility returns the ultrasound device to the manufacturer for service. A service technician can point a reader device at the ultrasound device to read a machine-readable indicator of the ultrasound device. Based on information obtained via the reading of the machine-readable indicator, the reader device (or any suitable device accessible to the service technician) can display a configuration setting of the ultrasound device. The configuration setting can completely determine the configuration of the ultrasound device, including software, firmware, and hardware configurations. The service technician can then procure a clone device to the ultrasound device, the clone device being configured according to the configuration setting to match the configuration of the ultrasound device. The service technician can then send the clone device to the care facility as a replacement to the ultrasound device. In some embodiments, the manufacturer does need to send a clone device to the care facility, but instead can update an existing ultrasound device at the care facility via a remote management system based on the configuration setting to match the ultrasound device that is under repair at the manufacturer. Hence, the care facility does not need to wait for the repair of the ultrasound device, but instead can receive immediately or with little delay a clone device that operates identically to the ultrasound device. The manufacturer is thus able to provide a level of service to the care facility that is not possible with conventional ultrasound systems.

Other uses of the ultrasound system 300 include guiding a user through an ultrasound protocol by displaying visual representations of the protocol steps. The visual representations can include portions of a medical worksheet, to assist a user in populating the medical worksheet. The ultrasound system 300 can anticipate a next step to be performed as part of an ultrasound examination, e.g., according to a protocol, and encode a trigger event into a machine-readable indicator on an ultrasound device so that when that machine-readable indicator is read, a visual representation is displayed that indicates the next step to be performed. The ultrasound system can determine the next step in any suitable way. In some embodiments, the ultrasound system includes a device to determine what the user is looking at, such as a camera pointing to the user or an eye-tracking device. For instance, to assist the user when the user is looking at a patient's name, the ultrasound system can encode a trigger event into a machine-readable indicator on an ultrasound device so that when that machine-readable indicator is read, a visual representation of a portion of a medical worksheet with a "Patient Name" field is displayed, such as on a touchscreen of the reader device. The user can then quickly and easily populate the "Patient Name" field. In some embodiments, the ultrasound system includes a speech recognition device, and the user can speak the patient's name (or any other suitable information for a field of a medical worksheet) to populate the field of the medical worksheet.

Figure 4:
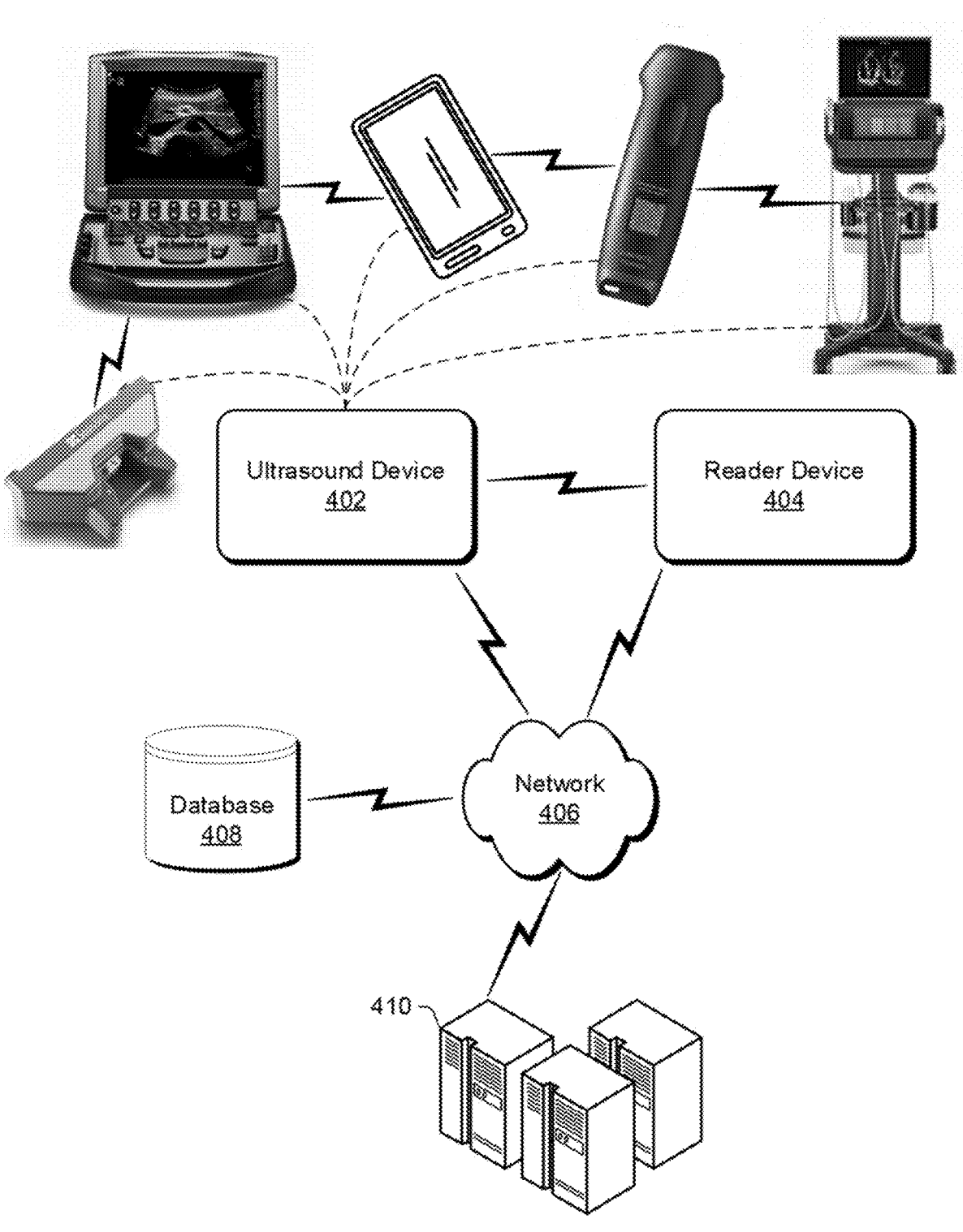
FIG. 4 illustrates an environment for an ultrasound system in accordance with some embodiments.

FIG. 4 illustrates an environment 400 for an ultrasound system in accordance with some embodiments. In some embodiments, the ultrasound system represents the ultrasound system 300 of FIG. 3, or other ultrasound system. The environment 400 includes an ultrasound device 402. The ultrasound device 302 of FIG. 3 is an example of the ultrasound device 402. Generally, the ultrasound device 402 can include any suitable device (e.g., a component of an ultrasound system) and any combinations thereof. Examples of the ultrasound device 402 (collectively, ultrasound devices 402) that are illustrated in FIG. 4 include a charging station, an ultrasound machine, a display device (e.g., a tablet or smartphone), an ultrasound scanner, and an ultrasound cart. Other examples include a transducer cable, a transducer cable holder, a docking station for an ultrasound machine, a scanner station configured to hold one or more ultrasound scanners, a needle guide, a battery for a wireless ultrasound scanner, a battery for an ultrasound machine, and the like.

Each of the ultrasound devices 402 can be in communication with one or more the other ultrasound devices 402, such as via a near field communication (NFC) link, a network (e.g., a local area network, wide area network, the network 406 (described below in more detail, etc.)), and the like. Further, each of the ultrasound devices 402 can be in communication with one or more of the other ultrasound devices 402 coupled by a cable or wire (e.g., wired), wirelessly, or a combination thereof.

The environment 400 also includes a reader device 404 that can be in communication with one or more of the ultrasound devices 402. The reader device 404 can be in communication with the ultrasound devices 402 wired, wirelessly, or a combination thereof. The reader device 404 includes a suitable reader, such as a camera, QR reader, barcode reader, laser, microphone, etc. configured to read a machine-readable indicator of the ultrasound devices 402. Moreover, the reader device 404 includes a sensor configured to determine a physical feature indicator of the ultrasound devices 402, such as a camera that can capture an image on an ultrasound device and a processor to determine the physical feature indicator from the image.

The ultrasound devices 402 and the reader device 404 are coupled to a network 406. The network 406 can include any suitable network, such as a local area network, a wide area network, a near field communication network, the Internet, an intranet, an extranet, a system bus that couples devices or device components (e.g., in an ASIC, FPGA, or SOC), and combinations thereof. Accordingly, in embodiments, information, such as device information that describes the ultrasound devices 402, can be communicated to the reader device 404 through an external network, i.e., network equipment that is external to the ultrasound devices 402 and the reader device 404 (e.g., a Wi-Fi network). Alternatively, information can be communicated between the reader device 404 and the ultrasound devices without passing the information through an external network. For instance, the information can be passed directly from the ultrasound devices 402 to the reader device 404 without network equipment that is external to the ultrasound devices 402 and the reader device 404.

The environment 400 also includes a database 408 that includes any suitable information for displaying data as described herein, such as displaying ultrasound device data in an augmented reality environment. Accordingly, the database 408 can include mappings of trigger events to display data for visual representations, as described above. The database 408 can include mappings for various ultrasound devices, device classes, device users, device owners, and device states, as disclosed herein. In an example, the database 408 provides one or more of the mappings to at least one of the ultrasound devices 402 and the reader device 404 via the network 406.

The environment 400 also includes a processor system 410 that can implement any of the functions described herein. The processor system 410 can be a separate device from the ultrasound device 402 and the reader device 404. Alternatively, the processor system 410 can be included in at least one of the ultrasound devices 402 and the reader device 404. In some embodiments, the processor system 410 and the database 408 are included in at least one of the ultrasound devices 402 and the reader device 404. In an example, the processor system 410 is implemented as part of a server system that is remote from (e.g., not collocated with) the ultrasound device 402 and the reader device 404.

Procedures

FIG. 5 illustrates a method 500 that can be performed by an ultrasound system in accordance with some embodiments. In some embodiments, the ultrasound system represents the ultrasound system 300, or other ultrasound system. The ultrasound system can include an ultrasound device, such as the ultrasound devices 302 and 402, a reader device, such as the reader devices 306 and 404, and a display device, such as the display device 316. Operations of the method are performed by processing logic that can comprise hardware (circuitry, dedicated logic, etc.), software (such as is run on a general-purpose computer system or a dedicated machine), firmware, or combinations thereof.

An ultrasound device exposes a machine-readable indicator at block 502. A reader device reads information from the machine-readable indicator at block 504. A display device displays device information about the ultrasound device based on the information read from the machine-readable indicator at block 506.

In some embodiments, the reader device includes the display device. For instance, the reader device can include a display screen, such as a touchscreen. Additionally or alternatively, the display device can display the device information in an augmented reality environment that is overlaid with the ultrasound device.

In some embodiments, the ultrasound device includes a display screen implemented to display the machine-readable indicator. The machine-readable indicator can include at least one of a quick response (QR) code, a bar code, an animation sequence, a pattern, and an image. Additionally or alternatively, the ultrasound device can include one or more light sources implemented to display the machine-readable indicator with light having a wavelength outside of the range of 380 nm to 740 nm.

In some embodiments, the device information indicates at least one of a cleaning status, an amount of remaining scan time, a battery level, and an examination type. Additionally or alternatively, the device information can indicate that the ultrasound device is paired with at least one of the reader device and the display device.

In some embodiments, the ultrasound system includes a scanner station configured to hold ultrasound scanners. The ultrasound device can include one of the ultrasound scanners, and the reader device can read the information from the machine-readable indicator while the ultrasound scanners are housed by the scanner station. The device information can recommend the one of the ultrasound scanners for an ultrasound examination.

FIG. 6 illustrates a method 600 that can be performed by an ultrasound system in accordance with some embodiments. In some embodiments, the ultrasound system represents the ultrasound system 300, or other ultrasound system. The ultrasound system can include an ultrasound device, such as the ultrasound devices 302 and 402, and a reader device, such as the reader devices 306 and 404, a memory, such as the databases 310 and 408, and a processor system, such as the processor systems 308 and 410. Operations of the method are performed by processing logic that can comprise hardware (circuitry, dedicated logic, etc.), software (such as is run on a general-purpose computer system or a dedicated machine), firmware, or combinations thereof.

A reader device reads information from machine-readable indicators of an ultrasound device at block 602. A memory stores, for the ultrasound device, a mapping of trigger events to display data at block 604. A processor system determines, based on the information read from the machine-readable indicator, a trigger event from the mapping at block 606. The processor system determines a visual representation of the display data from the mapping that corresponds to the trigger event at block 608. The processor system causes display of the visual representation at block 610.

In some embodiments, the ultrasound device includes an ultrasound scanner. The processor system can cause the display of the visual representation in an augmented reality environment that includes the ultrasound scanner. Additionally or alternatively, the reader device can include a display screen, and the processor system can cause the display of the visual representation on the display screen of the reader device, e.g., in an image environment that does not include an augmented reality environment.

In some embodiments, the ultrasound device includes a display screen implemented to display the machine-readable indicator as at least one of a quick response (QR) code, a bar code, an animation sequence, a pattern, and an image. Additionally or alternatively, the ultrasound device can include one or more light sources, implemented to display the machine-readable indicator with light having a wavelength outside of the range of 380 nm to 740 nm.

In some embodiments, the visual representation exposes a user manual for the ultrasound device. Additionally or alternatively, the visual representation can expose a medical worksheet. Additionally or alternatively, the visual representation can expose an indication of an ultrasound protocol step. Additionally or alternatively, the visual representation can expose directions for returning the ultrasound device when the ultrasound device is lost. Additionally or alternatively, the visual representation can expose a directional indicator to locate an additional ultrasound device that is paired with the ultrasound device, such as by displaying an arrow that points to the additional ultrasound device. Additionally or alternatively, the visual representation can expose an instructional video for operating the ultrasound device. Additionally or alternatively, the visual representation can expose a service order for servicing the ultrasound device.

In some embodiments, the reader device is implemented to capture a physical feature indication of the ultrasound device. The physical feature indication can indicate at least one of a shape of the ultrasound device, a size of the ultrasound device, a layout configuration of the ultrasound device, a number of buttons, knobs, or sliders on the ultrasound device, and a location of the ultrasound device relative to another device. The memory can store, for device classes corresponding to ultrasound devices, mappings of trigger events to display data. The processor system can determine, based on the physical feature indication, a device class for the ultrasound device, and select, based on the device class, the mapping for the ultrasound device from among the mappings stored by the memory.

In some embodiments, the memory is implemented to store, for workflow steps of the ultrasound device, mappings of trigger events to display data. The workflow steps can indicate a status of the ultrasound device, and include steps such as a charging step, a pairing step, a transportation step, an in-use step, and a cleaning step. The processor system can determine, based on at least one of an orientation of the ultrasound device, a location of the ultrasound device, a power use of the ultrasound device, and a connection status of the ultrasound device, a current workflow step from among the workflow steps for the ultrasound device. Based on the current workflow step, the processor system can then select the mapping from among the mappings stored by the memory.

Additionally or alternatively, the processor system can determine a user authentication level, and compare the user authentication level to a threshold authentication level. The processor system can cause the display of the visual representation based on an outcome of the comparison. For instance, if the user authentication level is greater than or equal to the threshold authentication level, then the processor system can cause the display of the visual representation. Else, if the user authentication level is less than the threshold authentication level, then the processor system can suppress the display of the visual representation.

FIG. 7 illustrates a method 700 that can be performed by an ultrasound device according to some embodiments. In some embodiments, the ultrasound device represents the ultrasound device 302, ultrasound device 402, or other ultrasound device. The ultrasound device can include a machine-readable indicator, such as the machine-readable indicator 304, an alert mechanism, such as a buzzer, vibrator, flashing light, speaker, etc., and a processor system, such as the processor systems 308 and 410. Operations of the method are performed by processing logic that can comprise hardware (circuitry, dedicated logic, etc.), software (such as is run on a general-purpose computer system or a dedicated machine), firmware, or combinations thereof.

The processor system determines, based on at least one of a location of the ultrasound scanner, a time since a previous use of the ultrasound scanner, and a use-calendar for the ultrasound scanner, a lost-scanner status of the ultrasound scanner at block 702. For instance, the location of the ultrasound scanner can indicate that the scanner is outside of a care facility, in a trash department of the care facility, outside a department in a care facility that owns the ultrasound scanner, etc. The ultrasound scanner can be a wireless ultrasound scanner. The time since a previous use of the ultrasound scanner can be compared to a threshold time since previous use (e.g., one week), and based on the comparison, the processor system can determine the lost-scanner status for the ultrasound scanner. For example, if the time since a previous use of the ultrasound scanner is greater than the threshold time, then the processor system can determine the ultrasound scanner is lost. The processor system can access the use-calendar for the ultrasound scanner, which can include a schedule for ultrasound scanner, e.g., the times reserved for use of the ultrasound scanner and the user or department who reserved the ultrasound scanner. If the ultrasound scanner is not located at a location for the time that it should be located at the location according to the use-calendar, then the processor system can determine the ultrasound scanner is lost. Additionally or alternatively, if the ultrasound scanner is not returned to a storage location within a time threshold (e.g., one hour) after a scheduled use according to the use-calendar, then the processor system can determine the ultrasound scanner is lost.

Based on the determination of the lost-scanner status, the processor system causes the alert mechanism to issue the user-perceivable alert at block 704. The issuing the user-perceivable alert can include causing a buzzer to buzz, causing a vibrator to vibrate, causing a light to flash or blink, causing a speaker to emit sound, combinations thereof, and the like.

Based on the determination of the lost-scanner status, the processor system causes display of the machine-readable indicator at block 706. The machine-readable indicator is configured to communicate an address for returning the ultrasound scanner. In some embodiments, the machine-readable indicator displays a uniform resource locator (URL) that displays content including the address for returning the ultrasound scanner. For instance, the address can be displayed on a web page for the URL. Additionally or alternatively, the machine-readable indicator can display a quick response (QR) code that directs a web browser to the URL.

FIG. 8 illustrates a method 800 that can be performed by an ultrasound system according to some embodiments. In some embodiments, the ultrasound system represents the ultrasound system 300, or other ultrasound system. The ultrasound system can include ultrasound devices, such as the ultrasound devices 302 and 402, and a reader device, such as the reader devices 306 and 404. Operations of the method are performed by processing logic that can comprise hardware (circuitry, dedicated logic, etc.), software (such as is run on a general-purpose computer system or a dedicated machine), firmware, or combinations thereof.

A reader device reads information from machine-readable indicators of ultrasound devices at block 802. Based on the information, the reader device displays a visual representation that recommends one of the ultrasound devices for an ultrasound examination at block 804.

In one example, the ultrasound system includes a scanner station configured to hold ultrasound scanners, and the ultrasound devices include the ultrasound scanners, as described above with respect to FIG. 2C. The reader device is implemented to read the information from the machine-readable indicators of the ultrasound scanners while the ultrasound scanners are housed by the scanner station. For instance, the reader device can read the information from the machine-readable indicators of the ultrasound scanners one ultrasound scanner at a time (e.g., sequentially). Alternatively, the reader device can read the information from the machine-readable indicators of the ultrasound scanners simultaneously for at least two of the ultrasound scanners. The information can indicate at least one of a cleaning status, an amount of remaining scan time, a battery level, and an examination type.

In some embodiments, the reader device is implemented to display the visual representation in an augmented reality environment that is overlaid with the one of the ultrasound devices. Additionally or alternatively, the reader device can display the visual representation in a display format that does not include an augmented reality environment.

In some embodiments, one or more of the ultrasound devices include display screens implemented to display the machine-readable indicators. At least one of the machine-readable indicators can include at least one of a quick response (QR) code, a bar code, an animation sequence, a pattern, and an image. Additionally or alternatively, one or more of the ultrasound devices can include one or more light sources implemented to display the machine-readable indicators with light having a wavelength outside of the range of 380 nanometers to 740 nanometers.

In some embodiments, the techniques to display data based on machine-reading of an ultrasound device as described herein can be used for non-clinical workflows, for example in the manufacturing/service environment for device identification and support. In some embodiments, the techniques to display data based on machine-reading of an ultrasound device as described herein can be used for clinical settings, for example, to support the device selection based on suitability for a clinical purpose. In some embodiments, the techniques to display data based on machine-reading of an ultrasound device as described herein can be used for communicating the device status (e.g., power, owner, "ready" state (damaged, not damaged, etc.)). In some embodiments, the amount of information related to the ultrasound device can be displayed based on a level of authorization. In some embodiments, the techniques to display data based on machine-reading of an ultrasound device as described herein can be used for ultrasound device identification, e.g., in a fleet of ultrasound devices, to identify the ultrasound device that is damaged. In some embodiments, the techniques to display data based on machine-reading of an ultrasound device as described herein can be used for non-physical device labeling, for example, ultrasound imaging using one or more neural networks. In some embodiments, the techniques to display data in an AR environment based on machine-reading of an ultrasound device as described herein can be used to provide feedback to the device maintenance team.

In some embodiments, the techniques to display data based on machine-reading of an ultrasound device as described herein can be used for clinical workflows, for example, in clinical imaging. For example, the persons are scanned using ultrasound and then vessel locations are displayed using a head-up display or phone. For example, an ultrasound scan is captured at one point in time and then the video/display the image is played back on the patient's anatomy in the future to allow past and present imaging data to be displayed on the person (e.g., displayed on their torso) or in the clinical environment (on a wall, in the air, etc.)

In some embodiments, the techniques to display data based on machine-reading of an ultrasound device as described herein can be used for clinical data recording/review, for example, to provide supplemental AR labeling/annotations, customized to the AR viewer's preferences, and not included on the primary clinical display, worksheet data entry/review, and the like. In some embodiments, the techniques to display data based on machine-reading of an ultrasound device as described herein can be used for education that involves for example, positioning/repositioning the scanner.

Embodiments of the techniques to display data based on machine-reading of an ultrasound device as described herein offer a simple, cost effective extensible way to show data in the same frame as the ultrasound device, minimize the need to develop a complex scanner display, allow for unforeseen (future) data (e.g., images, educational materials, guidance/instructions) to be offered to the customer.

Figure 9:
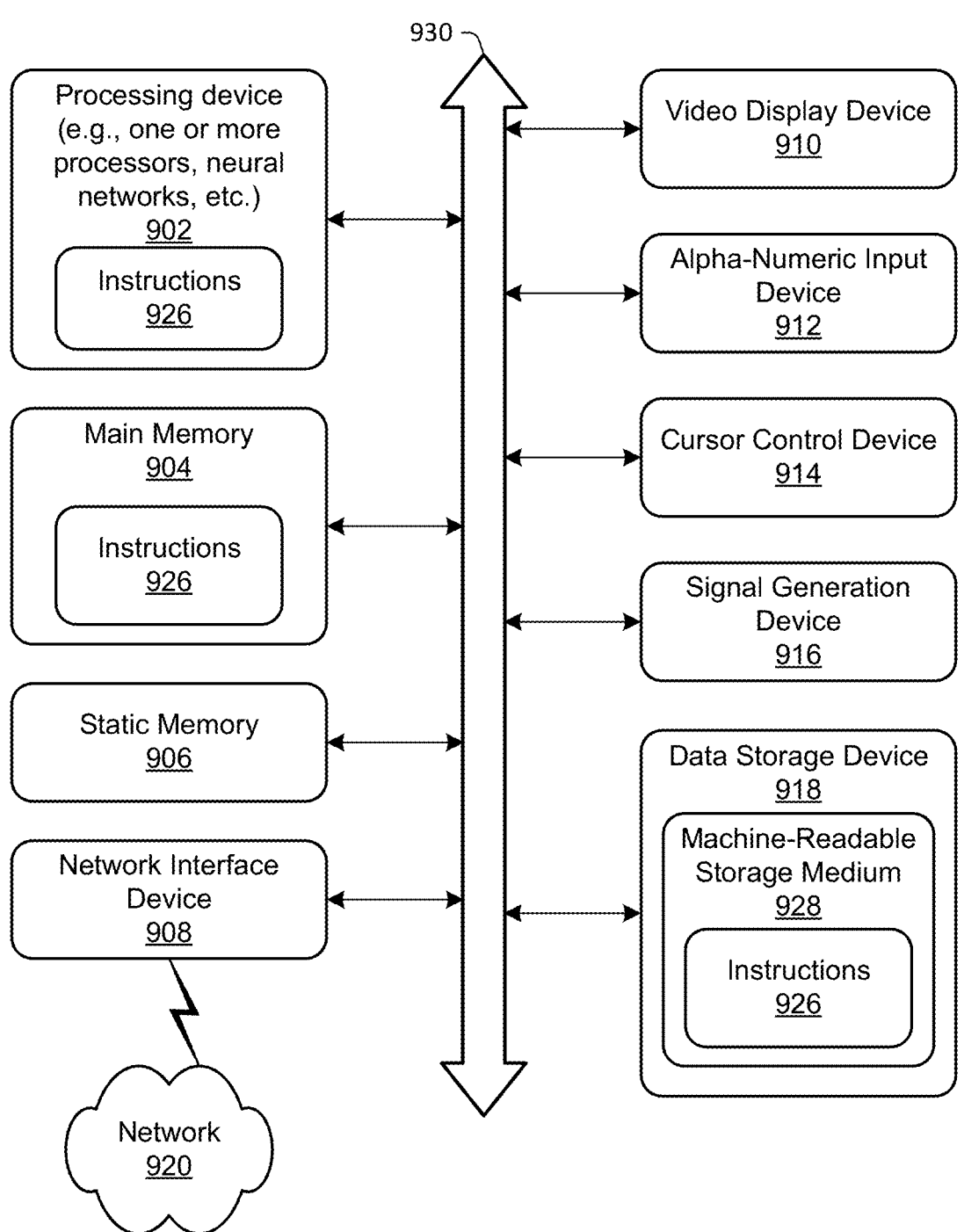
FIG. 9 illustrates a block diagram of an example computing device that can perform one or more of the operations described herein, in accordance with some embodiments.

FIG. 9 is a block diagram of an example computing device 900 that may perform one or more of the operations described herein, in accordance with some embodiments. Computing device 900 may be connected to other computing devices in a LAN, an intranet, an extranet, and/or the Internet. The computing device may operate in the capacity of a server machine in client-server network environment or in the capacity of a client in a peer-to-peer network environment. The computing device may be provided by a personal computer (PC), a server computing, a desktop computer, a laptop computer, a tablet computer, a smartphone, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods and processes discussed herein. In some embodiments, the computing device 900 may be one or more of an access point and a packet forwarding component.

The example computing device 900 may include a processing device (e.g., a general-purpose processor, a PLD, etc.) 902, a main memory 904 (e.g., synchronous dynamic random-access memory (DRAM), read-only memory (ROM)), a static memory 906 (e.g., flash memory and a data storage device 918), which may communicate with each other via a bus 930. Processing device 902 may be provided by one or more general-purpose processing devices such as a microprocessor, central processing unit, or the like. In an illustrative example, processing device 902 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 902 may also comprise one or more special-purpose processing devices such as an application specific integrated circuit (ASIC), a field programmable gate array (FPGA), a digital signal processor (DSP), network processor, or the like. The processing device 902 may be configured to execute the operations described herein, in accordance with one or more aspects of the present disclosure, for performing the operations and steps discussed herein.

Computing device 900 may further include a network interface device 908 which may communicate with a network 920. The computing device 900 also may include a video display unit 910 (e.g., a liquid crystal display (LCD) or a cathode ray tube (CRT)), an alphanumeric input device 912 (e.g., a keyboard), a cursor control device 914 (e.g., a mouse) and an acoustic signal generation device 916 (e.g., a speaker, and/or a microphone). In one embodiment, video display unit 910, alphanumeric input device 912, and cursor control device 914 may be combined into a single component or device (e.g., an LCD touch screen).

Data storage device 918 may include a computer-readable storage medium 928 on which may be stored one or more sets of instructions 926, e.g., instructions for carrying out the operations described herein, in accordance with one or more aspects of the present disclosure. For instance, the instructions 926 can implement the techniques for displaying data based on machine-reading of an ultrasound device, as described herein. Instructions 926 may also reside, completely or at least partially, within main memory 904 and/or within processing device 902 during execution thereof by computing device 900, main memory 904 and processing device 902 also constituting computer-readable media. The instructions may further be transmitted or received over a network 920 via network interface device 908.

While computer-readable storage medium 928 is shown in an illustrative example to be a single medium, the term "computer-readable storage medium" should be taken to include a single medium or multiple media (e.g., a centralized or distributed database and/or associated caches and servers) that store the one or more sets of instructions. In some embodiments, the computer-readable storage medium 928 implements the database of user-defined mappings, as described above. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

Unless specifically stated otherwise, terms such as "transmitting," "determining," "receiving," "generating," "or the like, refer to actions and processes performed or implemented by computing devices that manipulates and transforms data represented as physical (electronic) quantities within the computing device's registers and memories into other data similarly represented as physical quantities within the computing device memories or registers or other such information storage, transmission or display devices. Also, the terms "first," "second," "third," "fourth," etc., as used herein are meant as labels to distinguish among different elements and may not necessarily have an ordinal meaning according to their numerical designation.

Examples described herein also relate to an apparatus for performing the operations described herein. This apparatus may be specially constructed for the required purposes, or it may comprise a general-purpose computing device selectively programmed by a computer program stored in the computing device. Such a computer program may be stored in a computer-readable non-transitory storage medium, such as a storage memory.

The methods and illustrative examples described herein are not inherently related to any particular computer or other apparatus. Various general-purpose systems may be used in accordance with the teachings described herein, or it may prove convenient to construct more specialized apparatus to perform the required method steps. The required structure for a variety of these systems will appear as set forth in the description above.

The above description is intended to be illustrative, and not restrictive. Although the present disclosure has been described with references to specific illustrative examples, it will be recognized that the present disclosure is not limited to the examples described. The scope of the disclosure should be determined with reference to the following claims, along with the full scope of equivalents to which the claims are entitled.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

Various units, circuits, or other components may be described or claimed as "configured to" or "configurable to" perform a task or tasks. In such contexts, the phrase "configured to" or "configurable to" is used to connote structure by indicating that the units/circuits/components include structure (e.g., circuitry) that performs the task or tasks during operation. As such, the unit/circuit/component can be said to be configured to perform the task, or configurable to perform the task, even when the specified unit/circuit/component is not currently operational (e.g., is not on). The units/circuits/components used with the "configured to" or "configurable to" language include hardware—for example, circuits, memory storing program instructions executable to implement the operation, etc. Reciting that a unit/circuit/component is "configured to" perform one or more tasks, or is "configurable to" perform one or more tasks, is expressly intended not to invoke 35 U.S.C. 112, sixth paragraph, for that unit/circuit/component.

Additionally, "configured to" or "configurable to" can include generic structure (e.g., generic circuitry) that is manipulated by software and/or firmware (e.g., an FPGA or a general-purpose processor executing software) to operate in manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks. "Configurable to" is expressly intended not to apply to blank media, an unprogrammed processor or unprogrammed generic computer, or an unprogrammed programmable logic device, programmable gate array, or other unprogrammed device, unless accompanied by programmed media that confers the ability to the unprogrammed device to be configured to perform the disclosed function(s).

Reference in the specification to "one embodiment", "an embodiment", "one example", or "an example" means that a particular feature, structure, or characteristic described in conjunction with the embodiment can be included in at least one embodiment. The appearances of the phrases "in one embodiment" or "in an embodiment" in various places in the specification do not necessarily all refer to the same embodiment. The processes depicted in the figures that follow are performed by processing logic that comprises hardware (e.g., circuitry, dedicated logic, etc.), software, or a combination of both. Although the processes are described below in terms of some sequential operations, it should be appreciated that some of the operations described may be performed in a different order. Moreover, some operations may be performed in parallel rather than sequentially.

In the specification, the term "and/or" describes three relationships between objects that may exist. For example, A and/or B may represent the following cases: only A exists, both A and B exist, and only B exist, where A and B may be singular or plural.

The foregoing description, for the purpose of explanation, has been described with reference to specific embodiments. However, the illustrative discussions above are not intended to be exhaustive or to limit embodiments to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and are not to be limited to the details given herein, but may be modified within the scope and equivalents of the appended claims.

What is claimed is:

1. An ultrasound system comprising:
an ultrasound device having a machine-readable indicator;
a reader device configured to read information from the machine-readable indicator;
a display device configured to display device information about the ultrasound device based on the information read from the machine-readable indicator; and
a scanner station configured to hold ultrasound scanners, wherein the ultrasound device includes one of the ultrasound scanners, wherein the reader device is implemented to read the information from the machine-readable indicator while the ultrasound scanners are housed by the scanner station, wherein the device information recommends the one of the ultrasound scanners for an ultrasound examination.

2. The ultrasound system as described in claim 1, wherein the reader device includes the display device.

3. The ultrasound system as described in claim 1, wherein the display device is implemented to display the device information in an augmented reality environment that is overlaid with the ultrasound device.

4. The ultrasound system as described in claim 1, wherein the ultrasound device includes a display screen implemented to display the machine-readable indicator including at least one of a quick response (QR) code, a bar code, an animation sequence, a pattern, and an image.

5. The ultrasound system as described in claim 1, wherein the ultrasound device includes one or more light sources implemented to display the machine-readable indicator with light having a wavelength outside of the range of 380 nanometers to 740 nanometers.

6. The ultrasound system as described in claim 1, wherein the device information indicates at least one of a cleaning status, an amount of remaining scan time, a battery level, and an examination type.

7. The ultrasound system as described in claim 1, wherein the device information indicates that the ultrasound device is paired with at least one of the reader device and the display device.

8. An ultrasound system comprising:
an ultrasound device having a machine-readable indicator;
a reader device configured to read information from the machine-readable indicator;
a memory storing, for the ultrasound device, a mapping of trigger events to display data; and
a processor system configured to:
determine, based on the information read from the machine-readable indicator, a trigger event from the mapping;
determine a visual representation of the display data from the mapping that corresponds to the trigger event; and
cause display of the visual representation, wherein the visual representation exposes at least one of a user manual for the ultrasound device, a medical worksheet, an indication of an ultrasound protocol step, directions for returning the ultrasound device when lost, a directional indicator to locate an additional ultrasound device that is paired with the ultrasound device, an instructional video for operating the ultrasound device, and a service order for servicing the ultrasound device.

9. The ultrasound system as described in claim 8, wherein the ultrasound device includes an ultrasound scanner, and the processor system is implemented to cause the display of the visual representation in an augmented reality environment that includes the ultrasound scanner.

10. The ultrasound system as described in claim 8, wherein the ultrasound device includes an ultrasound scanner, the reader device includes a display screen, and the processor system is implemented to cause the display of the visual representation on the display screen of the reader device.

11. The ultrasound system as described in claim 8, wherein the ultrasound device includes a display screen or one or more light sources, the display screen implemented to display the machine-readable indicator as at least one of a quick response (QR) code, a bar code, an animation sequence, a pattern, and an image, the one or more light sources implemented to display the machine-readable indicator with light having a wavelength outside of the range of 380 nanometers to 740 nanometers.

12. An ultrasound system comprising:

an ultrasound device having a machine-readable indicator;

a reader device configured to read information from the machine-readable indicator;

a memory storing, for the ultrasound device, a mapping of trigger events to display data; and a processor system configured to:

determine, based on the information read from the machine-readable indicator, a trigger event from the mapping;

determine a visual representation of the display data from the mapping that corresponds to the trigger event; and cause display of the visual representation, wherein the reader device is implemented to capture a physical feature indication of the ultrasound device, wherein the memory is implemented to store, for device classes corresponding to ultrasound devices, mappings of trigger events to display data, and wherein the processor system is implemented to:

determine, based on the physical feature indication, a device class for the ultrasound device; and select, based on the device class, the mapping for the ultrasound device from among the mappings stored by the memory.

13. The ultrasound system as described in claim 12, wherein the physical feature indication indicates at least one of a shape of the ultrasound device, a size of the ultrasound device, a layout configuration of the ultrasound device, a number of buttons, knobs, or sliders on the ultrasound device, and a location of the ultrasound device relative to another device.

14. An ultrasound system comprising:

an ultrasound device having a machine-readable indicator;

a reader device configured to read information from the machine-readable indicator;

a memory storing, for the ultrasound device, a mapping of trigger events to display data; and a processor system configured to:

determine, based on the information read from the machine-readable indicator, a trigger event from the mapping;

determine a visual representation of the display data from the mapping that corresponds to the trigger event; and cause display of the visual representation, wherein the memory is implemented to store, for workflow steps of the ultrasound device, mappings of trigger events to display data, and wherein the processor system is implemented to:

determine, based on at least one of an orientation of the ultrasound device, a location of the ultrasound device, a power use of the ultrasound device, and a connection status of the ultrasound device, a current workflow step from among the workflow steps for the ultrasound device; and select, based on the current workflow step, the mapping from among the mappings stored by the memory.

15. The ultrasound system as described in claim 14, wherein the workflow steps include a charging step, a pairing step, a transportation step, an in-use step, and a cleaning step.

16. An ultrasound system comprising:

an ultrasound device having a machine-readable indicator;

a reader device configured to read information from the machine-readable indicator;

a memory storing, for the ultrasound device, a mapping of trigger events to display data; and a processor system configured to:

determine, based on the information read from the machine-readable indicator, a trigger event from the mapping;

determine a visual representation of the display data from the mapping that corresponds to the trigger event; and cause display of the visual representation, wherein the processor system is implemented to:

determine a user authentication level; and compare the user authentication level to a threshold authentication level, wherein said cause display of the visual representation is based on an outcome of said compare.

17. An ultrasound scanner comprising:

a machine-readable indicator displayable on an external surface of the ultrasound scanner;

an alert mechanism configured to issue a user-perceivable alert; and a processor system configured to:

determine, based on at least one of a location of the ultrasound scanner, a time since a previous use of the ultrasound scanner, and a use-calendar for the ultrasound scanner, a lost-scanner status of the ultrasound scanner;

cause, based on the determination of the lost-scanner status, the alert mechanism to issue the user-perceivable alert; and cause, based on the determination of the lost-scanner status, display of the machine-readable indicator, the machine-readable indicator configured to communicate an address for returning the ultrasound scanner.

18. The ultrasound scanner as described in claim 17, wherein the machine-readable indicator displays at least one of a uniform resource locator (URL) and quick response (QR) code that directs a web browser to the URL, the URL implemented to display content that includes the address for returning the ultrasound scanner.

* * * * *